ns011426094B2

United States Patent
Trzasko (10) Patent No.: US 11,426,094 B2
(45) Date of Patent: Aug. 30, 2022

(54) METHODS FOR ITERATIVE RECONSTRUCTION OF MEDICAL IMAGES USING PRIMAL-DUAL OPTIMIZATION WITH STOCHASTIC DUAL VARIABLE UPDATING

(71) Applicant: Mayo Foundation for Medical Education and Research, Rochester, MN (US)

(72) Inventor: Joshua D. Trzasko, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 399 days.

(21) Appl. No.: 16/498,973

(22) PCT Filed: Apr. 6, 2018

(86) PCT No.: PCT/US2018/026417
§ 371 (c)(1),
(2) Date: Sep. 27, 2019

(87) PCT Pub. No.: WO2018/187662
PCT Pub. Date: Oct. 11, 2018

(65) Prior Publication Data
US 2021/0085208 A1    Mar. 25, 2021

Related U.S. Application Data

(60) Provisional application No. 62/482,290, filed on Apr. 6, 2017.

(51) Int. Cl.
*A61B 5/055* (2006.01)
*G01R 33/56* (2006.01)
(Continued)

(52) U.S. Cl.
CPC .......... *A61B 5/055* (2013.01); *G01R 33/5608* (2013.01); *G01R 33/5611* (2013.01); *G06F 17/10* (2013.01)

(58) Field of Classification Search
CPC .......................... A61B 5/055; G01R 33/5608; G01R 33/5611; G06F 17/10
See application file for complete search history.

(56) References Cited

U.S. PATENT DOCUMENTS

| 9,460,557 B1* | 10/2016 | Tran | G06T 11/005 |
| | | | 382/131 |
| 2015/0363947 A1* | 12/2015 | Rigie | G06T 11/005 |
| | | | 382/131 |

(Continued)

OTHER PUBLICATIONS

Zhanxing Zhu and Amos J. Storkey, Adaptive Stochastic Primal-Dual Coordinate Descent for Separable Saddle Pointe Problems, ECML/PKDD, Jun. 12, 2015 (Year: 2015).*

(Continued)

*Primary Examiner* — G. M. A Hyder
(74) *Attorney, Agent, or Firm* — Quarles & Brady LLP (57) ABSTRACT

Methods for reconstructing images of a subject from data acquired with a medical imaging system, such as a magnetic resonance imaging ("MRI") system, are described. In general, the image reconstructions implement a primal-dual optimization strategy that, in each iteration, stochastically updates a dual variable.

19 Claims, 3 Drawing Sheets

(51) Int. Cl.
G01R 33/561 (2006.01)
G06F 17/10 (2006.01)

(56) References Cited

U.S. PATENT DOCUMENTS

2016/0178720 A1* 6/2016 Mailhe .............. G01R 33/5611
324/309
2016/0367212 A1* 12/2016 Tang ................. G01R 33/5611
324/309

OTHER PUBLICATIONS

Patrick L Combettes and Jean-Christophe Pesquet, Stochastic Forward-Backward and Primal-Dual Approximation Algorithm With Applications To Online Image Restoration, 2016 24th European Signal Processing Conference (EUSIPCO) (Year: 2016).*
Bertsekas D. P. Incremental gradient, subgradient, and proximal methods for convex optimization: A survey. Optimization for Machine Learning 2010:1-38.
Cai J-F. et al. Fast Singular Value Thresholding without Singular Value Decomposition. Methods and Applications of Analysis 2013;20:335-352.
Candes E.J. et al. Unbiased risk estimates for singular value thresholding and spectral estimators. IEEE Trans Sig Proc 2013;61:4643-4657.
Chambolle A. et al. A first-order primal-dual algorithm for convex problems with applications to imaging. J Math Imag Vis 2011;40:120-45.
Coifman RR et al. Translation invariant denoising. Wavelets and Statistics, Springer Lecture Notes, 103, Springer-Verlag, Berlin, 1995.
Figueiredo M.A.T. et al. An EM algorithm for wavelet-based image restoration. IEEE Trans Imag Proc. 2003;12:906-16.
Guerquin-Kern M. et al. A fast wavelet-based reconstruction method for magnetic resonance imaging. IEEE Trans Med Imag 2011;30:1649-60.
Kamilov U. Parallel proximal methods for total variation minimization. Proc. ICASSP 2016;4697-4701.
Shin P. J. et al. Calibrationless parallel imaging reconstruction based on structured low-rank matrix completion. MRM 2014;72:959-70.
Trzasko J et al. CLEAR: Calibration-free parallel imaging using locally low-rank encouraging reconstruction. Proc. ISMRM 2012;517.
Vasanawala SS et al. Improved pediatric MR imaging with compressed sensing. Radiology 2010;256:607-16.
International Search Report and Written Opinion from parent PCT/US2018/026417, dated Jun. 29, 2018, 12 pages.
Knoll, et al., Joint MR-PET reconstruction using vector valued Total Generalized Variation, Proceedings of the International Society for Magnetic Resonance in Medicine, 23rd Annual Meeting & Exhibition, No. 3424, May 15, 2015, p. 3424.
Mehranian, et al., 3D TV-Based Compressed MR Image Reconstruction Using a Primal Dual Algorithm, Proceedings of the International Society for Magnetic Resonance in Medicine, 20th Annual Meeting & Exhibition, May 5, 2012 (May 5, 2012), p. 4228.
Zhu, et al., Adaptive Stochastic Primal-Dual Coordinate Descent for Separable Saddle Point Problems, In: Machine Learning and Knowledge Discovery in Databases, European Conference, ECML PKDD 2015, Proceedings, Part I, Sep. 7, 2015 (Sep. 7, 2015), Springer, Porto, Portugal, XP055486054, ISBN: 978-3-319-23527-1, pp. 645-658.
Trzasko, et al., Local versus Global Low-Rank Promotion in Dynamic MRI Series Reconstruction, Proceedings of the International Society for Magnetic Resonance in Medicine, 19th Annual Meeting & Exhibition, May 7, 2011 (May 7, 2011), p. 4371.
Trzasko, et al., Stochastic Primal-Dual Optimization for Locally Low-Rank MRI Reconstruction: A Stable Alternative to Cycle Spinning, Proceedings of the International Society for Magnetic Resonance in Medicine, 25th Annual Meeting & Exhibition, No. 455, Apr. 7, 2017.
Zhang, et al., Stochastic Primal-Dual Coordinate Method for Regularized Empirical Risk Minimization, Proceedings of the 32nd International Conference On Machine Learning, Jul. 6, 2015, pp. 353-361.

* cited by examiner

METHODS FOR ITERATIVE RECONSTRUCTION OF MEDICAL IMAGES USING PRIMAL-DUAL OPTIMIZATION WITH STOCHASTIC DUAL VARIABLE UPDATING

CROSS-REFERENCE TO RELATED APPLICATIONS

This application is a 371 U.S. national phase application from PCT/US2018/026417, filed Apr. 6, 2018, which claims the benefit of U.S. Provisional Patent Application Ser. No. 62/482,290, filed on Apr. 6, 2017, and entitled "METHODS FOR ITERATIVE RECONSTRUCTION OF MEDICAL IMAGES USING PRIMAL-DUAL OPTIMIZATION WITH STOCHASTIC DUAL VARIABLE UPDATING," each of which is herein incorporated by reference in its entirety.

STATEMENT REGARDING FEDERALLY SPONSORED RESEARCH

This invention was made with government support under CIF1318347 awarded by the National Science Foundation. The government has certain rights in the invention.

BACKGROUND

Penalized regression is widely used for solving inverse problems that arise in signal and image reconstruction, processing, and analysis. Motivated by both theoretical and empirical arguments that leveraging redundant a priori knowledge during an estimation task can lead to performance improvements, it is increasingly common for the cost functionals underlying such estimation frameworks to include multiple penalty or regularization functionals. For instance, modern signal and image estimation processes, such as those that underlie iterative medical image reconstruction (e.g., MRI, CT, PET/SPECT, ultrasound), often make use of multiple penalty or regularization functions to promote certain properties in a target estimation quantity. Examples applications include translation invariant wavelet-based deconvolution, local and non-local patch-based image denoising, and locally low-rank ("LLR") magnetic resonance image reconstruction. Several machine learning paradigms (e.g., support vector machines (SVM) and trained reaction diffusion networks (TRDN)) are also based on multi-penalty regression models.

Variable splitting is commonly utilized to decouple and isolate the functional components of a multi-penalty regression model, and to enable known analytical properties about their individual structure to be exploited. Example solvers that employ this paradigm include: alternating direction method of-multipliers ("ADMM"), composite splitting, majorization-minimization, parallel proximal gradient ("PPG"), and primal-dual hybrid gradient ("PDHG") iteration. By design, the structure of these and related algorithms typically includes directly (i.e., non-iteratively) solving at each iteration a set of subproblems possessing closed-form analytical solutions. This property simplifies their implementation and tuning.

Although variable splitting-based multi-penalty regression algorithms are relatively efficient, there are scenarios for which their runtime complexity remains impractically high—such as when the number of penalty terms, K, is large, or subproblem solving is computationally expensive. For example, consider image-domain calibrationless MRI reconstruction from partial Fourier phased array data, where the aggregate penalty is the sum of nuclear norms of small matrices associated with individual image pixels. If the target result is an 8-channel 256×256 image set, and block size B=5 is used for matrix construction, then a typical variable splitting algorithm for this problem will nominally require computing K=63,504 singular value decompositions ("SVD") of size 25×8 matrices during each iteration. While these operations are small and independent, their number and non-triviality leads such algorithms to have high overall complexity.

Depending on the problem structure and executing hardware architecture, parallel computing can partially mitigate these computational expenses. For the above example, penalty task parallelization on an 8-core x86 processor with two-fold simultaneous multithreading ("SMT") can reduce the algorithm's per-iteration time complexity to roughly $K_{eff}$=3,969 SVDs. While significant, this reduction may be insufficient for time-sensitive applications like clinical medical imaging.

Due to its efficiency and other properties, primal-dual hybrid gradient ("PDHG") iteration is an attractive deterministic optimization algorithm for convex multi-penalty regression. This method generally augments an Arrow-Horrowitz iteration with an extrapolation gradient step on either the primal or dual variable to enable fast, universal convergence.

A stochastic variant of PDHG ("SPDHG") is an appealing strategy for computationally challenging multi-penalty regression problems in imaging, and is a potential numerically stable alternative to heuristic cycle-spinning algorithms. However, two barriers that may inhibit the broad adoption of SPDHG exist. First, the convergence of PDHG is now routinely asserted using standard Fejér monotonicity; however, asserting SPDHG convergence remains highly technical. To make SPDHG broadly accessible, asserting its general convergence using the same basic toolset as PDHG would be beneficial. Second, although SPDHG has been demonstrated for imaging applications, the specific advantage of this technique for applications where the plurality of penalties is the dominant source of computational expense has not been clearly demonstrated. Corresponding, the viability, setup, and potential benefits of adopting SPDHG for such applications in lieu of cycle spinning is not broadly recognized.

As one specific example, in calibration-less parallel MR image reconstruction, an ensemble of low-rank penalties targeting small image blocks can be used. Similarly, multiple spatially shifted wavelet transforms may be utilized simultaneously to achieve translation invariance. One advantage of using multiple penalties is that certain signal or image redundancies, such as those that arise when using overlapping spatial blocks in an LLR reconstruction model, can be exploited for the purpose of achieving higher quality reconstructed images. However, problems with multiple penalty functions are also generally much harder for a computer to solve than traditional forms. One common heuristic, based on a technique called cycle spinning, entails only working with a small and typically random subset of the penalties at each iteration of an iterative reconstruction process.

While this heuristic does reduce computation time significantly, it suffers from a number of practical issues ranging from inconsistency with the originally defined reconstruction problem, residual image artifacts, and often a failure of the iterative algorithm to stably converge.

SUMMARY OF THE DISCLOSURE

The present disclosure addresses the aforementioned drawbacks by providing a method for producing an image of a subject from data acquired with a medical imaging system. Data acquired from a subject using the medical imaging system are provided to a computer system. An image of the subject is reconstructed by inputting the provided data to an iterative reconstruction algorithm implemented with a hardware processor and memory of the computer system in order to iteratively reconstruct the image from the data. The iterative reconstruction algorithm implements a primal-dual optimization that in each iteration stochastically updates at least one dual variable of the primal-dual optimization. Without loss of generality, the medical imaging system may be a magnetic resonance imaging ("MRI") system.

It is another aspect of the present disclosure to provide a signal reconstruction unit implemented with a hardware processor and a memory. The memory has stored thereon data acquired from an object with a measurement system, and the hardware processor is in electrical communication with the memory. The hardware processor is configured to reconstruct a signal from the stored data by inputting the data to a multi-penalty objective function and iteratively optimizing the multi-penalty objective function in a primal domain and a dual domain. In each iteration a stochastic update is performed in the dual domain. The signal reconstruction unit also includes a display that receives and displays the reconstructed signal. The reconstructed signal provides a representation of the object from which the data were acquired.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here is a method for reconstructing images from data acquired with a medical or other imaging system, such as a magnetic resonance imaging ("MRI") system, based on a multi-penalty regression problem. The image reconstruction implements an optimization paradigm that, like cycle spinning, works with subsets of a penalty set at each iteration to improve computation time. In the methods described in the present disclosure, the optimization of the image reconstruction works with subsets of the penalty set at each iteration in a manner that ensures mathematical consistency with the target reconstruction, and does so in a way that circumvents issues with residual artifacts and poor convergence.

Multiple penalty (e.g., K-penalty) regression problems can generally be described as, $$[\hat{X}] = \arg\min_{X} \left\{ \sum_{k=1}^{K} \mathcal{P}_k(\Psi_k\{X\}) + \mathcal{Q}(X) \right\}; \tag{1}$$

where X represents the target multi-dimensional signal, which may be real-valued or complex-valued; $\Psi_k(\bullet)$ is a linear operator; and $\mathcal{P}_k(\bullet)$ and $\mathcal{Q}(\bullet)$ are both (possibly non-smooth) convex functionals. As noted above, in lieu of attacking the problem in Eqn. (1), variable splitting is commonly utilized to decouple and isolate its K+1 functional components, and to enable known analytical properties about their individual structure to be exploited.

Unlike other approaches, the reconstruction problems used in the methods of the present disclosure are generalized into a primal-dual form, in which the reconstruction problem is solved two different ways with the intent that the solutions converge to one another. This variable updating can be performed in parallel, in serial, or in a hybrid paradigm. Stochastic estimation techniques are used within the secondary (i.e., dual) domain to reduce computational overhead. Because randomization occurs in this secondary domain, overall algorithmic convergence or solution validity is not compromised.

As described here, a primal-dual optimization strategy for multi-penalty regression problems, such as signal and image reconstructions, is provided. By stochastically updating the dual variable of such optimizations, the computational advantage of cycle spinning can be achieved, but without the introduction of artifacts and instability in convergence. Thus, the primal-dual optimization techniques described in the present disclosure can be implemented for multi-penalty medical image reconstruction problems, as well as non-medical signal and image problems, including but not limited to wavelet-based signal denoising and deconvolution where a bank of temporally translated wavelets is used for sparse signal modeling. In one example, the multi-penalty regression problem can include an LLR reconstruction from data acquired with a medical or other imaging system.

Examples of mathematical conventions that can be used when describing the methods described in the present disclosure are provided. Let $\mathcal{F}(X)$: dom$\{\mathcal{F}\} \to \mathbb{R}^+$ be a proper, lower semicontinuous, convex functional that maps a real-valued or complex-valued multi-dimensional signal, X, onto the (non-negative) real number line. By definition, $\forall \{X,Z\} \in \text{dom}\{\mathcal{F}\}$ and $\forall \theta \in [0,1]$, $\mathcal{F}$ satisfies, $$\mathcal{F}(\theta X + (1-\theta)Z) \le \theta \mathcal{F}(X) + (1-\theta)\mathcal{F}(Z) \tag{2}.$$

The dual of $\mathcal{F}$, which may also be referred to as the Legendre-Fenchel transform or convex conjugate, evaluated at $Y \in \text{dom}\{\mathcal{F}^*\}$, can be defined as, $$\mathcal{F}^*(Y) = \max_X \{\text{Re}(\langle X, Y \rangle) - \mathcal{F}(X)\}; \tag{3}$$

where Re(•) isolates the real component of a complex signal, and $\langle \cdot, \cdot \rangle$ denotes an inner product.

To ensure that the methods developed herein are viable for both real-valued and complex-valued estimation tasks, all differential operations can be performed using Wirtinger calculus conventions. That is, for a complex variable $X = X_r + jX_i$ with $j = \sqrt{-1}$.

$$\frac{\partial}{\partial X} = \frac{1}{2}\left(\frac{\partial}{\partial X_r} - j\frac{\partial}{\partial X_i}\right); \tag{4}$$

$$\frac{\partial}{\partial \overline{X}} = \frac{1}{2}\left(\frac{\partial}{\partial X_r} + j\frac{\partial}{\partial X_i}\right). \tag{5}$$

For consistency with this calculus, the subdifferential (e.g., the set of all subgradients) of a real-valued functional of either a real or complex variable can be described as, $$\partial \mathcal{F}(X) = \{G \in \text{dom}\{\mathcal{F}\} \mid \mathcal{F}\{X_0\} \geq \mathcal{F}(X) + 2\text{Re}(\langle G, X_0 - X \rangle), \forall X_0 \in \text{dom}\{\mathcal{F}\}\} \tag{6}$$

For smooth functionals, Eqn. (6) contains a single element equal to the conjugate Wirtinger derivative in Eqn. (5).

Because a convex functional can be expressed in terms of its dual, Eqn. (1) can be equivalently stated as, $$[\hat{X}] = \arg\min_X \max_{Y_{[1,K]}} \{\mathcal{J}(X, Y_{[1,K]})\}; \tag{7}$$

where $Y_{[1,K]} = \{Y_1, \ldots, Y_K\}$ and the cost functional, $$\mathcal{J}(X, Y_{[1,K]}) = \sum_{k=1}^{K} (\text{Re}(\langle Y_k, \Psi_k\{X\}\rangle) - \mathcal{P}_k^*(Y_k)) + \mathcal{Q}(X). \tag{8}$$

The optimality conditions for this saddle point problem are, $$0 \in \frac{1}{2}\sum_{k=1}^{K} \Psi_k^*\{Y_{k,\star}\} + \partial \mathcal{Q}(X_\star); \tag{9}$$

$$0 \in \frac{1}{2}\Psi^*\{X_\star\} - \partial \mathcal{P}_k^*(Y_{k,\star}); \tag{10}$$

where *{•} denotes the adjoint of a linear operator and #8b is understood for all $k \in [1, K]$.

By defining $\Lambda$ and $\Gamma_k$ as positive definite diagonal (linear) preconditioners, Eqns. (9) and (10) reveals the following resolvent-based fixed point identities, $$X_\star = (I + \Lambda \partial \mathcal{Q})^{-1}\left\{X_\star - \frac{1}{2}\sum_{k=1}^{K} \Lambda\{\Psi_k^*\{Y_{k,\star}\}\}\right\}; \tag{11}$$

$$Y_{k,\star} = (I + \Gamma_k \partial \mathcal{P}_k^\circ)^{-1}\left\{Y_{k,\star} + \frac{1}{2}\Gamma_k\{\Psi_k\{X_\star\}\}\right\}. \tag{12}$$

These identities describe that it is possible under appropriate conditions to iteratively estimate X and $Y_{[1, K]}$ with variable updating performed in parallel (e.g., Jacobi), serially (e.g., Gauss-Seidel), or a hybrid paradigm, any of which can be an instance of the following generic iterative scheme:

$$X_{t+1} = (I + \Lambda \partial \mathcal{Q})^{-1}\left\{X_t - \frac{1}{2}\sum_{k=1}^{K} \Lambda\{\Psi_k^*\{Y_{k,t}\}\}\right\}; \tag{13}$$

$$Y_{k,t+1} = (I + \Gamma_k \partial \mathcal{P}_k^*)^{-1}\left\{Y_{k,t} + \frac{1}{2}\Gamma_k\{\Psi_k\{X_{t+1} + \theta(X_{t+1} - X_t)\}\}\right\}; \tag{14}$$

where $t \in \mathbb{Z}^+$ and $\theta \in \mathbb{R}$ are the iteration number and update model parameter, respectively. An extrapolation gradient step, or steps, could also be applied on the dual variable, or variables.

Although Eqns. (13) and (14) are straightforward to execute and solve Eqn. (1) exactly, if K is large or the penalties functionals are nontrivial to apply, this method can be computationally expensive to perform. One opportunity for reducing the per-iteration complexity of Eqns. (13) and (14) in such scenarios is to only update a small subset (e.g., a "mini-batch") of the dual variables at each iteration. This paradigm can be achieved through the following stochastic generalization of (14), $$Y_{k,t+1} = (I + \eta_{k,t}\Gamma_k \partial \mathcal{P}_k^\circ)^{-1}\left\{Y_{k,t} + \frac{\eta_{k,t}}{2}\Gamma_k\{\Psi_k\{X_{t+1} + \theta(X_{t+1} - X_t)\}\}\right\}; \tag{15}$$

where $\eta_{k,t} \in \{0, 1\}$ is an iteration-wise parameter that indicates whether or not a dual variable should be updated at iteration t. As one example, $\eta_{k,t}$ may be a wide-sense stationary ("WSS") binary random process with universally positive expectation (e.g., $\mathbb{E}[\eta_{k,t}] \in (0, 1]$).

Without loss of generality, it can be assumed in some implementations that the generating mechanism for these indicators is constrained such that $\forall_t \geq 0$, $$\sum_{k=1}^{K} \eta_{k,t} \geq 1. \tag{16}$$

When the complexity of Eqns. (13) and (14) is dominated by constituent operations of the dual variable updates, adopting the stochastic update rule in Eqn. (15) can provide an approximate $(\mathbb{E}[\eta_{k,t}])^{-1}$ reduction in the per iteration computational cost, which can provide a potentially significant savings.

In some instances, the index set $[1, K] \subseteq \mathbb{Z}^+$ can be partitioned into G non-overlapping groups, or "mini-batches," which can be denoted as $\Omega_g$ with $g \in [1, G]$, such that, $$\bigcup_{g=1}^{G} \Omega_g = \bigcup_{g=1}^{G}\bigcup_{k \in \Omega_g} k = [1, K]. \tag{17}$$

It is contemplated that in some embodiments, implementing a group-wise homogeneous indicator activation, and allowing only one group to be active during each iteration, may offer a practical advantage.

The following example demonstrates application of the stochastic primal-dual framework of the present disclosure for use with an LLR-regularized MRI image reconstruction. Persons having ordinary skill in the art will appreciate how this framework can be applied to other MRI and other medical image modality applications, as well as other regularization and constraint models. In a standard MRI exam, the measured k-space data, G, can be described as:

$$G = A\{F\} + N \quad (18);$$

where F is the target image series, $A\{\ldots\}$ is the (linear) forward operator, and N is zero mean complex Gaussian noise. LLR reconstruction includes solving the following convex optimization problem:

$$X_{LLR} = \underset{X}{\operatorname{argmin}}\left\{J(X) \triangleq \lambda \sum_{b \in \Omega} \|R_b X\|_* + \|A\{X\} - G\|_F^2\right\}; \quad (19)$$

where $\Omega$ represents the set of all overlapping blocks; $R_b$ is a block selection operator; $\|\ldots\|_*$ and $\|\ldots\|_F$ are the nuclear and Frobenius norms, respectively; and $\lambda$ is a regularization parameter. As one example, Eqn (19) can be solved via parallel proximal gradient (PPG) iteration, $$X_{t+1} = P_{LLR}\{\tau\lambda\}\{t\}(X_t - \tau A^*\{A\{X_t\} - G\}) \quad (20);$$

where $P_{LLR}\{\tau\lambda\}\{t\}(\ldots)$ is a pseudo-prox functional for the LLR penalty. As one example, the pseudo-prox functional can be a blockwise singular value thresholding ("SVT") operator, $$P_{LLR}\{\tau\lambda\}\{t\}(Z) = \left(\sum_{b \in \Lambda_t} R_b^* R_b\right)^{-1} \sum_{b \in \Lambda_t} R_b^* SVT_{\tau\lambda/2}\{R_b Z\}; \quad (21)$$

where $\Lambda_t \subseteq \Omega$ is the set of block considered at iteration, t. Although employing the entire blockset (i.e., $\Lambda_t = \Omega$) is mathematically preferred, as SVTs are the computational bottleneck of Eqn. (21), in practice $\Lambda_t$ is typically defined as a non-overlapping subset set of $\Omega$ that is randomly shifted each iteration, t. However, with this setup image intensities have been observed to subtly oscillate between iterations. Due to instantaneous use of non-overlapping blocksets, thresholding artifacts can also manifest at block boundaries.

To overcome these challenges, the methods described in the present disclosure recast the LLR optimization in a manner where stochastic acceleration can still be used, but in a more stable manner.

To start, recall that the dual of the nuclear norm is, $$\|Z\|_* = \max_{\|Y\|_2 \leq 1} \{Re\{Tr\{Y^* Z\}\}\}; \quad (22)$$

where $\|\ldots\|_2$ denotes the spectral norm. Eqn. (20) can thus be equivalently stated as a saddle point optimization:

$$X_{LLR} = \underset{X}{\operatorname{argmin}} \max_{\forall b \in \Omega, \|Y_b\|_2 \leq \lambda/2}\left\{\sum_{b \in \Omega} 2Re\{Tr\{Y_b^* R_b X\}\} + \|A\{X\} - G\|_F^2\right\}; \quad (23)$$

where $Y_b$ are dual variables. This primal-dual problem can be solved using, amongst other strategies, a Chambolle-Pock iteration, $$X_{t+1} = (\tau A^* A + I)^{-1}\left(\tau A^*\{G\} + X_t - \sum_{b \in \Omega} R_b^* Y_{b,t}\right); \quad (24)$$

where $$Y_{b,t+1} = P_{\|\cdot\|_2 \leq \frac{\lambda}{2}}(Y_{b,t} + \sigma_b R_b(2X_t - X_{t-1})); \quad (25)$$

and where $\tau$ and $\sigma_b$ are step sizes, and $$P_{\|\cdot\|_2 \leq \frac{\lambda}{2}}(\ldots)$$

is a singular value clipping operator. Unlike PPG, Eqns. (24) and (25) are capable of exactly solving Eqn. (18); however, in this form, where all dual variables are updated each iteration, it does not offer significant computational advantages over non-cycle-spinning PPG. To increase computational efficiency, a random subset (i.e., "mini-batch") of the dual variables can be updated each iteration, analogous to cycle spinning. Formally, this is achieved by replacing the dual update in Eqn. (25) with, $$Y_{b,t+1} = (1 - \eta_{b,t})Y_{b,t} + \eta_{b,t} P_{\|\cdot\|_2 \leq \frac{\lambda}{2}}(Y_{b,t} + \sigma_b R_b(2X_t - X_{t-1})); \quad (26)$$

Where $\eta_{b,t}$ are Bernoulli random variables. Practically, it can be advantageous to use a single $\eta_{b,t}$ for a same disjoint block sets, as used in cycle spinning, with probability of $1/N_S$, where $N_S$ is the number of sets that completely tile the image domain. Because stochastic approximation is used in the dual rather than primal (i.e., image) domain, and the base iteration on which this is derived is exact, it is contemplated that this stochastic primal-dual ("SPD") strategy for LLR, and other image reconstruction or image processing applications, will have a more stable convergence than PPG, and will in turn generate images with fewer visual artifacts.

Figure 1:
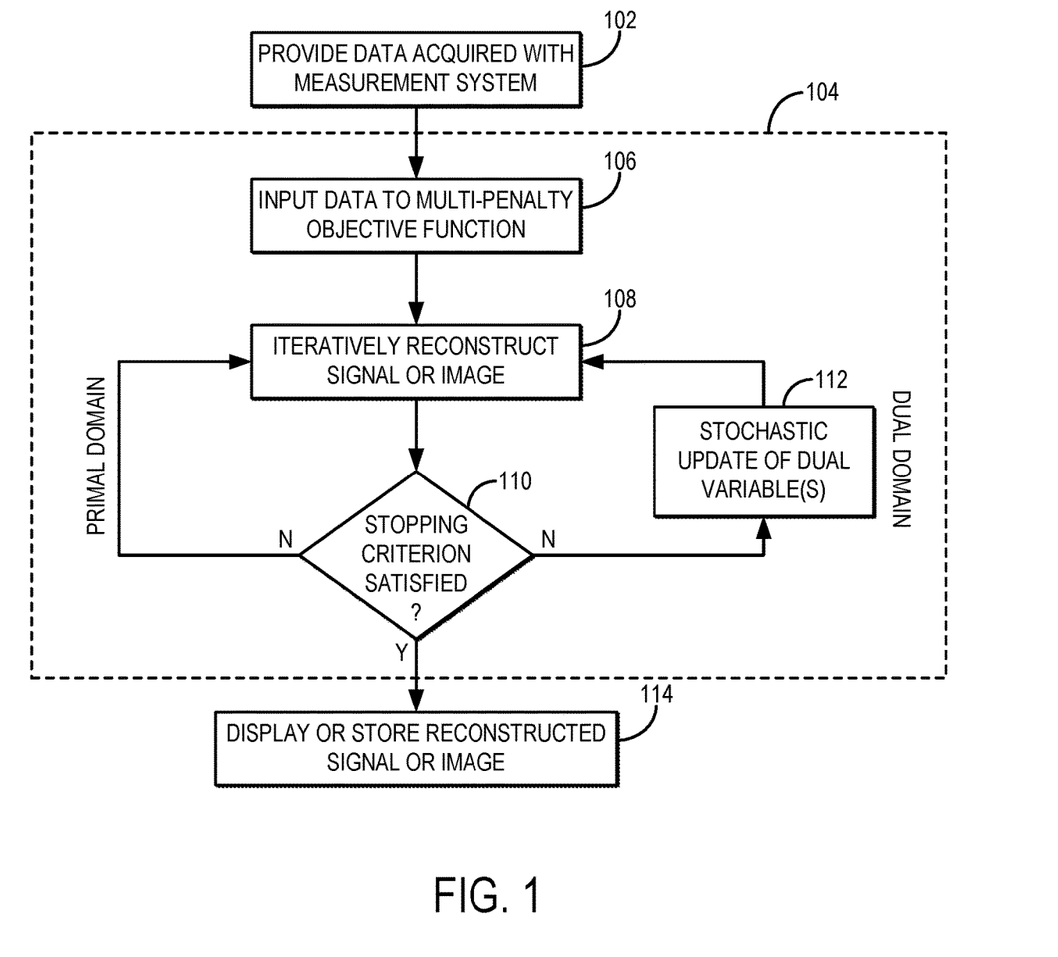
FIG. 1 is a flowchart setting forth the steps of an example method for reconstructing a signal or an image from data acquired with a measurement system by iteratively optimizing a multi-penalty objective function in a primal domain and a dual domain, in parallel, while updating in the dual domain in each iteration using a stochastic update.

Referring now to FIG. 1, a flowchart is illustrated as setting forth the steps of an example method for reconstructing a signal or image from data acquired with a measurement system, such as a medical imaging system, which may include a magnetic resonance imaging ("MRI") system. The method includes providing data acquired with a measurement system to a computer system, as indicated at step 102. As one example, providing the data can include retrieving previously acquired data from a memory or other data storage. As another example, providing the data can include acquiring the data with the measurement system. For instance, the data can be magnetic resonance data that are acquired with an MRI system and providing the data to the computer system can include acquiring the data with the MRI system.

The data are then processed by the computer system, such as by a hardware processor residing in the computer system, to reconstruct a signal or an image therefrom, as indicated generally at block 104. The reconstruction generally includes inputting the data to an objective function, which is preferably a multi-penalty objective function, as indicated at step 106. This objective function is then iteratively optimized as indicated at step 108 and the loop determined by decision block 110. In each iteration the objective function is optimized in both a primal domain and a dual domain. In some implementations, the objective function is optimized in both the primal domain and the dual domain in parallel. In other implementations, the objective function is serially optimized in the primal and dual domains. In still other implementations, a hybrid scheme is used to optimize the object function in both the primal and dual domains. As indicated at step 112, a stochastic update is performed in the dual domain in each iteration. This implementation reduces computational overhead of the reconstruction. Because randomization can occur in the dual domain in some implementations, the overall algorithmic convergence or solution validity is not compromised.

When a stopping criterion is satisfied, as determined at decision block 110, the reconstruction process is completed and the reconstructed signal or image is provided as an output. As indicated at step 114, the reconstructed signal or image, which provides a representation of the underlying object from which the data were acquired, can be displayed to a user on a display, or can be stored for later use or processing.

Figure 2:
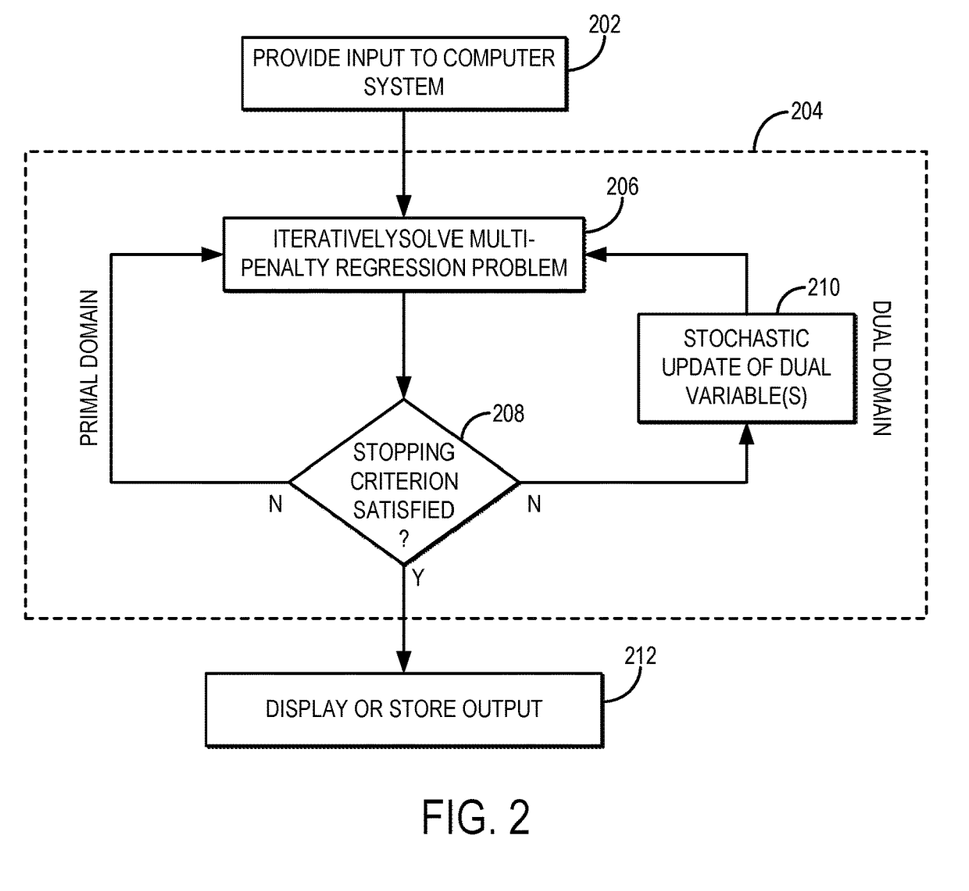
FIG. 2 is a flowchart setting forth the steps of an example method for solving a multi-penalty regression problem using a stochastic primal-dual algorithm implemented with a hardware processor and a memory.

More generally, referring to FIG. 2, a flowchart is illustrated as setting forth the steps of an example method for solving a multi-penalty regression problem using a stochastic primal-dual algorithm implemented with a hardware processor and a memory. The method includes providing an input to a computer system, as indicated at step 202. The input can be any suitable data or other input to the multi-penalty regression problem to be optimized or otherwise solved. As one example, the input can be data acquired with a measurement system, as described above. Such data can include data acquired with a medical imaging system or other imaging system. The input can be provided by retrieving previously input data or other information that has been stored in a memory or other suitable data storage. The input can also be provided by querying an input device with the computer system. For instance, the input can be provided by querying a measurement device or other suitable input device using the computer system in order to retrieve data or other information from the input device.

In some embodiments, the multi-penalty regression problem can be a reconstruction problem for reconstructing an image from data acquired with a measurement system, such as a medical imaging system or other imaging system.

In some other embodiments, the multi-penalty regression problem can be an image processing problem for processing an image to improve the quality of that image. For instance, the image processing problem can be a denoising problem, such that the processed image output by the stochastic primal-dual algorithm is a denoised image.

In still other embodiments, the multi-penalty regression problem can be implemented in a machine learning algorithm, which may include a support vector machine ("SVM"), a neural network, a trained reaction diffusion network ("TRDN"), or other suitable machine learning algorithm. In these instances, the stochastic primal-dual optimization described in the present disclosure can be used when constructing or otherwise implementing these machine learning algorithms, which incorporate one or more multi-penalty regression problems. As a non-limiting example, a machine learning algorithm can be constructed for reconstructing an image from data acquired with a measurement system based in part on a multi-penalty regression problem. In such an example, the stochastic primal-dual optimization methods described in the present disclosure can be used, such as by implementing the stochastic primal-dual optimization as a layer in the machine learning algorithm.

The provided input is used as an input to the selected multi-penalty regression problem, which is optimized or otherwise solved using a stochastic primal-dual algorithm implemented with a hardware processor and memory of the computer system, as indicated generally at block 204. The multi-penalty regression problem is then iteratively optimized as indicated at step 206 and the loop determined by decision block 208. In each iteration the multi-penalty regression problem is optimized in both a primal domain and a dual domain. In some implementations, the multi-penalty regression problem is optimized in both the primal domain and the dual domain in parallel. In other implementations, the multi-penalty regression problem is serially optimized in the primal and dual domains. In still other implementations, a hybrid scheme is used to optimize the multi-penalty regression problem in both the primal and dual domains.

As indicated at step 210, a stochastic update is performed in the dual domain in each iteration. This implementation reduces computational overhead of the reconstruction. Because randomization can occur in the dual domain in some implementations, the overall algorithmic convergence or solution validity is not compromised.

When a stopping criterion is satisfied, as determined at decision block 208, the optimization process is completed and the output of the optimized, or otherwise solved, multi-penalty regression problem is provided as an output. As indicated at step 210, the output can be displayed to a user on a display, or can be stored for later use or processing.

Figure 3:
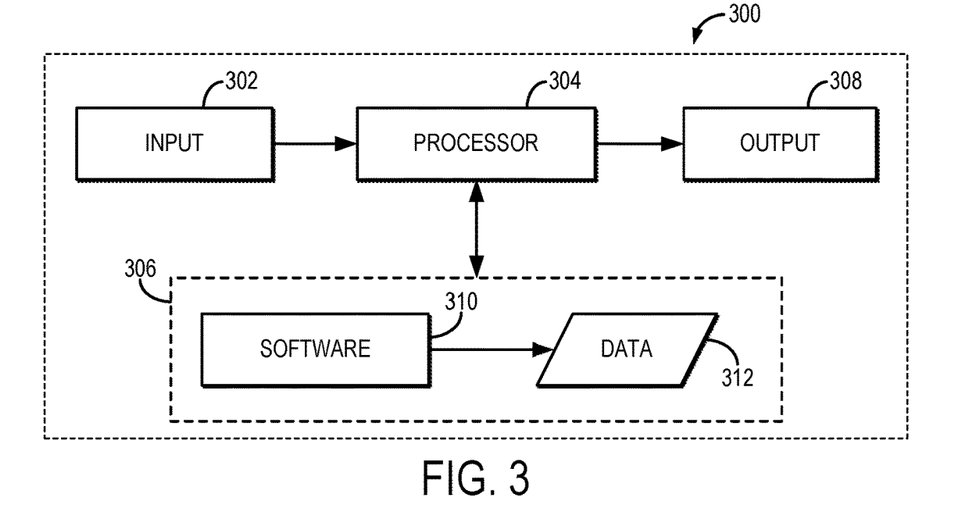
FIG. 3 is a block diagram of an example signal reconstruction unit implemented by a hardware processor and a memory, which can perform the reconstruction methods described in the present disclosure.

Referring now to FIG. 3, a block diagram of an example of a signal reconstruction unit 300 that can perform the methods described in the present disclosure is shown. The signal reconstruction unit 300 is generally implemented with a hardware processor 304 and a memory 306.

The signal reconstruction unit 300 includes an input 302, at least one hardware processor 304, a memory 306, and an output 308. The signal reconstruction unit 300 can also include any suitable device for reading computer-readable storage media. The signal reconstruction unit 300 may be implemented, in some examples, a workstation, a notebook computer, a tablet device, a mobile device, a multimedia device, a network server, a mainframe, or any other general-purpose or application-specific computing device. The signal reconstruction unit 300 may operate autonomously or semi-autonomously, or may read executable software instructions from the memory 306 or a computer-readable medium (e.g., a hard drive, a CD-ROM, flash memory), or may receive instructions via the input 302 from a user, or any another source logically connected to a computer or device, such as another networked computer or server. In general, the signal reconstruction unit 300 is programmed or otherwise configured to implement the methods and algorithms described above.

The input 302 may take any suitable shape or form, as desired, for operation of the signal reconstruction unit 300, including the ability for selecting, entering, or otherwise specifying parameters consistent with performing tasks, processing data, or operating the signal reconstruction unit 300. In some aspects, the input 302 may be configured to receive data, such as data acquired with a measurement system from an object. Such data may be processed as described above to reconstruct a signal or an image, which may be a two-dimensional or three-dimensional image. In addition, the input 302 may also be configured to receive any other data or information considered useful for reconstructing a signal or image from the data acquired with the measurement system using the methods described above.

Among the processing tasks for operating the signal reconstruction unit 300, the at least one hardware processor 304 may also be configured to carry out any number of post-processing steps on data received by way of the input 302.

The memory 306 may contain software 310 and data 312, such as data acquired with a measurement system, and may be configured for storage and retrieval of processed information, instructions, and data to be processed by the at least one hardware processor 304. In some aspects, the software 310 may contain instructions directed to reconstructing signals or images from the data acquired with a measurement system.

In addition, the output 308 may take any shape or form, as desired, and may be configured for displaying, in addition to other desired information, reconstructed signals or images.

Figure 4:
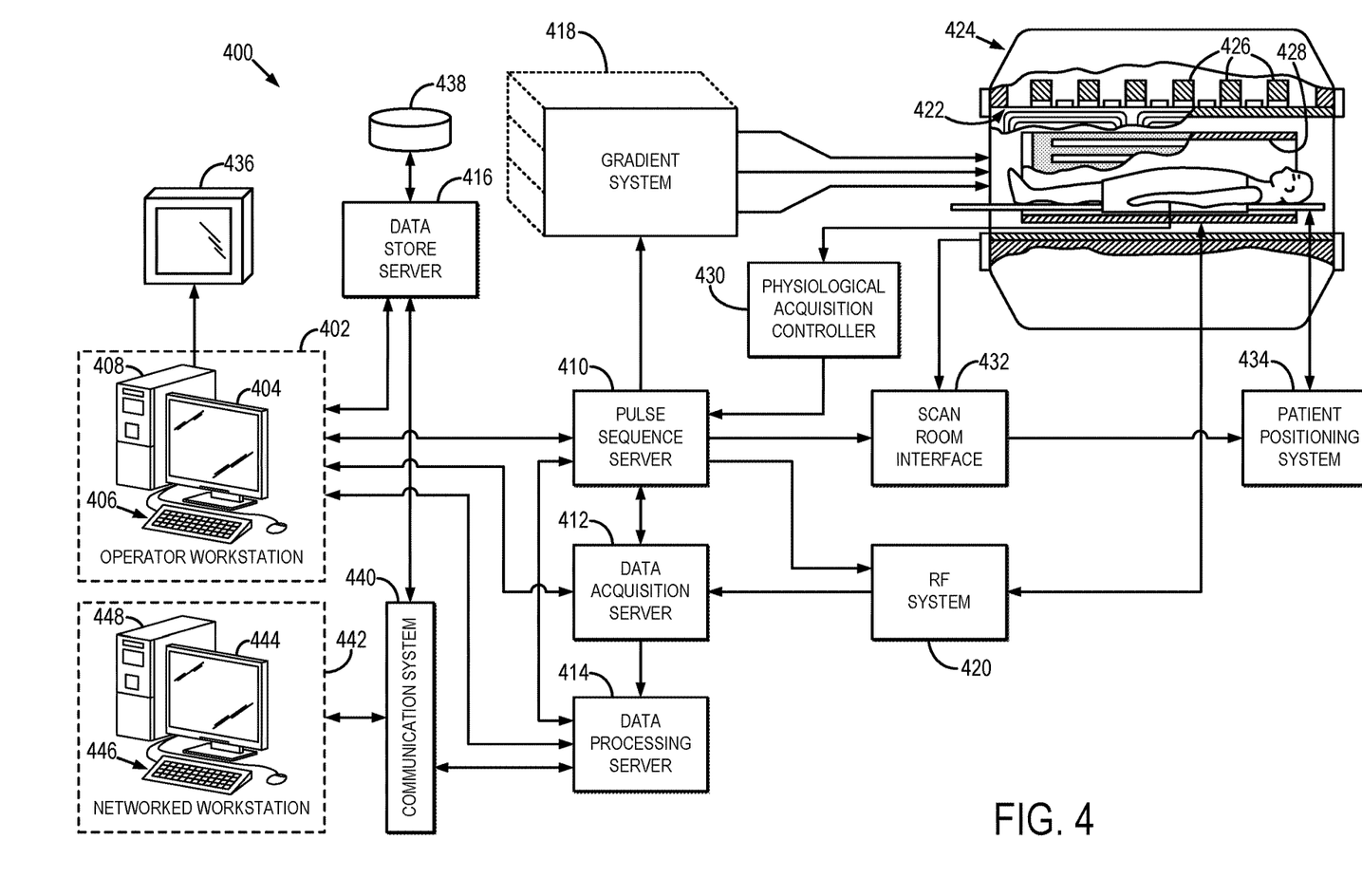
FIG. 4 is a block diagram of an example magnetic resonance imaging ("MRI") system that can be used to acquire magnetic resonance data and to implement the methods described in the present disclosure.

Referring particularly now to FIG. 4, an example of an MRI system 400 that can implement the methods described here is illustrated. The MRI system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MRI system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections.

The pulse sequence server 410 functions in response to instructions provided by the operator workstation 402 to operate a gradient system 418 and a radiofrequency ("RF") system 420. Gradient waveforms for performing a prescribed scan are produced and applied to the gradient system 418, which then excites gradient coils in an assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (27);$$

and the phase of the received magnetic resonance signal may also be determined according to the following relationship:

$$\varphi = \tan^{-1}\left(\frac{Q}{I}\right). \qquad (28)$$

The pulse sequence server 410 may receive patient data from a physiological acquisition controller 430. By way of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data is not lost by data overrun. In some scans, the data acquisition server 412 passes the acquired magnetic resonance data to the data processor server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MRI system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

The present disclosure has described one or more preferred embodiments, and it should be appreciated that many equivalents, alternatives, variations, and modifications, aside from those expressly stated, are possible and within the scope of the invention.

The invention claimed is:

1. A method for producing an image of a subject from data acquired with a medical imaging system, the steps of the method comprising:
    (a) providing to a computer system, data acquired from a subject using a medical imaging system;
    (b) reconstructing an image of the subject with the computer system by inputting the provided data to an iterative reconstruction algorithm implemented with a hardware processor and a memory of the computer system in order to iteratively reconstruct the image from the data, wherein the iterative reconstruction algorithm implements a primal-dual optimization that in each iteration stochastically updates at least one dual variable of the primal-dual optimization; and
    wherein the iterative reconstruction algorithm is a multi-penalty iterative reconstruction algorithm.

2. The method as recited in claim 1, wherein the multi-penalty iterative reconstruction algorithm is a locally low rank image reconstruction algorithm.

3. The method as recited in claim 1, wherein the multi-penalty iterative reconstruction algorithm is a sparsity-promoting image reconstruction algorithm.

4. The method as recited in claim 1, wherein the multi-penalty iterative reconstruction algorithm includes at least one of mixed regularization or mixed penalty types.

5. The method as recited in claim 1, wherein a random subset of the dual variables is updated in each iteration.

6. The method as recited in claim 1, wherein a subset of the dual variables is updated in each iteration according to a predetermined schedule.

7. The method as recited in claim 1, wherein providing the data to the computer system comprises acquiring the data from the subject with the medical imaging system and communicating the data from the medical imaging system to the computer system.

8. The method as recited in claim 1, wherein the medical imaging system is a magnetic resonance imaging (MRI) system.

9. The method as recited in claim 1, wherein reconstructing the image of the subject with the computer system comprises iteratively optimizing an objective function in both a primal domain and a dual domain.

10. The method as recited in claim 9, wherein iteratively optimizing the objective function in both the primal domain and the dual domain comprises optimizing the objective function in parallel in the primal domain and the dual domain.

11. A signal reconstruction unit comprising:
    a memory having stored thereon data acquired from an object with a measurement system;
    a hardware processor in electrical communication with the memory, the hardware processor being configured to reconstruct a signal from the stored data by inputting the data to a multi-penalty objective function and iteratively optimizing the multi-penalty objective function in a primal domain and a dual domain, wherein in each iteration a stochastic update is performed in the dual domain; and
    a display that receives and displays the reconstructed signal, wherein the reconstructed signal provides a representation of the object from which the data were acquired.

12. The signal reconstruction unit as recited in claim 11, wherein the hardware processor is configured to perform the stochastic update on a random subset of dual variables in the dual domain.

13. The signal reconstruction unit as recited in claim 11, wherein the hardware processor is configured to perform the stochastic update on a subset of the dual variables in the dual domain according to a predetermined update schedule stored in the memory.

14. The signal reconstruction unit as recited in claim 11, wherein the multi-penalty objective function is a locally low rank objective function.

15. The signal reconstruction unit as recited in claim 11, wherein the multi-penalty objective function is a sparsity-promoting objective function.

16. The signal reconstruction unit as recited in claim 11, wherein the multi-penalty objective function includes at least one of mixed regularization or mixed penalty types.

17. The signal reconstruction unit as recited in claim 11, wherein the measurement system is a medical imaging system, and the reconstructed signal comprises one of a two-dimensional or three-dimensional image of the object.

18. The signal reconstruction unit as recited in claim 17, wherein the medical imaging system is a magnetic resonance imaging (MRI) system.

19. The signal reconstruction unit as recited in claim 11, wherein the hardware processor is configured to iteratively optimize the multi-penalty objective function in parallel in the primal domain and the dual domain.

* * * * *